United States Patent [19]

Mikkelsen

[11] Patent Number: Plant 5,256

[45] Date of Patent: Jul. 10, 1984

[54] KALANCHOE PLANT NAMED FORTYNINER

[75] Inventor: James C. Mikkelsen, Ashtabula, Ohio

[73] Assignee: Mikkelsens, Inc., Ashtabula, Ohio

[21] Appl. No.: 422,522

[22] Filed: Sep. 23, 1982

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A hybrid Kalanchoe cultivar named Fortyniner having deep yellow flower color, strong compact growth, floriferous and uniform flowering habit, excellent keeping qualities, and an adaptability with the use of growth regulators to commercial production in 9 to 15 cm. containers.

1 Drawing Figure

The present invention relates to a new and distinctive cultivar of kalanchoe plant, botanically known as kalanchoe, and referred to by the cultivar name Fortyniner. The new cultivar was developed by me through controlled breeding by crossing seedling 76-561-17 (seed parent)×seedling 78-965-9 (pollen parent). Asexual reproduction by stem cuttings has shown that the unique features of this new kalanchoe are stabilized and are reproduced true to type in successive propagations.

The following characteristics distinguish Fortyniner from both its parent cultivars and other cultivated kalanchoes of this type known and used in the floriculture industry:

1. In comparison to Gelbe Melody U.S. Plant Pat. No. 3,854, Yellow Nugget U.S. Plant Pat. No. 4,726 and Firefly U.S. Plant Pat. No. 4,728, the flower color of Fortyniner is more uniform, flower keeping qualities are improved, flower quantity and placement are improved, plant growth is more reliable, especially in adverse light environments, and flowering is 5–7 days faster in winter months.

2. The three cultivars noted above all have an apparent genetic abnormality relating to foliar malformations, which presumably was transmitted in breeding from Gelbe Melody, a contributing parent to Nugget and Firefly. A dominant leaf characteristic of these cultivars was the development of an adventitious growth out of the leaf mid-rib area resembling a cockscomb. My new cultivar, having little Gelbe Melody lineage, is free of this problem.

3. The size, shape, and margin of the foliage of Fortyniner most closely resembles the cultivar Firefly.

4. Gelbe Melody, Yellow Nugget, and Firefly grow quite slowly in dark periods and thus produce fewer and poorer quality cuttings. Fortyniner has greater productivity under the same environments.

5. Fortyniner has an overall better flower-to-plant proportion than the three above named cultivars.

6. As illustrated, flowering develops over a considerable length of time from the earliest flowering to the opening of the last buds.

7. The self branching habit of Fortyniner is much more pronounced than in the above three named cultivars, often flowering at the lowest node near the soil level.

8. Flower quality is above average in all seasons. The florets appear to be more resistant to botrytis petal blight than the other named cultivars.

9. Fortyniner tends to be more compact with closer internodes, and thus needs less applications of growth regulators than the other named cultivars, and is readily adaptable to commercial production in 9–15 cm. containers.

The accompanying colored photograph taken in March 1982 illustrates in perspective view the overall appearance of Fortyniner grown in a 10 cm. plastic pot, and showing the colors as true as it is reasonably possible to obtain in a colored reproduction of this type.

The following is a detailed description of Fortyniner based on plants produced under commercial practices in the greenhouses of Mikkelsens, Inc., Ashtabula, Ohio. Color references are made to The Royal Horticultural Society Colour Chart except where general terms of ordinary dictionary significance are used.

PARENTAGE

A designed and controlled cross of seedling #76-561-17 as the seed parent and #78-965-9 as the pollen parent.

PROPAGATION

Type cutting: Short tip cutting with stems 2 cm. long.

Time to root: 10–12 Days at 21° C. night temperature, summer; 14–16 days at 21° C. night temperature, winter.

Rooting habit: Abundant, fibrous, dendritic.

PLANT DESCRIPTION

Form: Upright compact semi-bushy succulent plant.

Habit of growth: Upright, self branching, close internodes with moderate rate of growth for kalanchoes.

Foliage: Leaves are simple, opposite, slightly convex at base of plant, to flat, then to slightly concave at apex of plants; symmetrical.

(1) *Size.*—As illustrated, 60 to 65 mm. wide by 10 mm. long. Size can be greater when grown in larger pots and/or given more space. p2 (2) *Shape.*—Ovate to elliptic, apex obtuse, base obtuse, little if any twisting.

(3) *Texture.*—Glabrous, coriaceous, succulent.

(4) *Margin.*—Crenate.

(5) *Color.*—Young foliage top side, green 137A-B, under side, green 137-C. Mature foliage top side, yellow green 147-A; underside, yellow green 147B-C.

FLOWERING DESCRIPTION

Flowering habits: Inflorescence of each shoot is formed by dichotomous branching, starting with opening of terminal flower of main axis, followed by terminal flowers of the side branches, and continuing as illustrated with subsequent development of branches in the inflorescence.

Natural flowering season: Late December, early January. Flowering time under controlled day-length at 20° C. night temperature in summer is 8–9 weeks; in winter, 12–13 weeks. Flowering times can vary depending on the amount of light energy available.

Flower buds: Elliptical to oblong, symmetrical, up to 6–7 mm. long before opening, becoming tubular with petals sheathed with four green sepals.

Flowers borne: On compound dichasial cymes. Peduncles quite vigorous, flower pedicels strong, length of both readily controlled with growth regulators.

Quantity of flowers: Highly floriferous, with individual terminal cymes having up to 75 or more initiated buds. Excellent self branching adds to the number of potential cymes that can bloom.

Petals:

(1) *Shape.*—Nearly round, top cuspidate.

(2) *Color.*—Top side: when opening, yellow near 17B, fading to yellow 16A then to 16B. Under side: yellow 16C.

(3) *Number of petals.*—4, United in corolla, salver form: 6–7 mm. in diameter, total floret diameter 15–16 mm.

Reproductive organs:

(1) *Stamens.*—8 In number (2 pairs of 4). Anther shape: flat, elliptical, color yellow. Filament color: translucent green. Pollen color: light yellow.

(2) *Pistils.*—Stigma shape: flat, crystalline, color white. Style color: light green. Ovaries: four (4) in number, celled, size 7 mm. long, color green.

DISEASE RESISTANCE

To date appears to be resistant to powdery mildew and botrytis petal blight; does not show genetic malformations on the foliage.

I claim:

1. A new and distinct cultivar of Kalanchoe plant known by the cultivar name Fortyniner, as described and illustrated, and particularly characterized by its deep yellow flower color, floriferous and uniform flowering habit, strong compact growth with excellent self branching, excellent keeping qualities, and by its adaptability with the use of growth regulators to commercial production in 9–15 cm. containers.

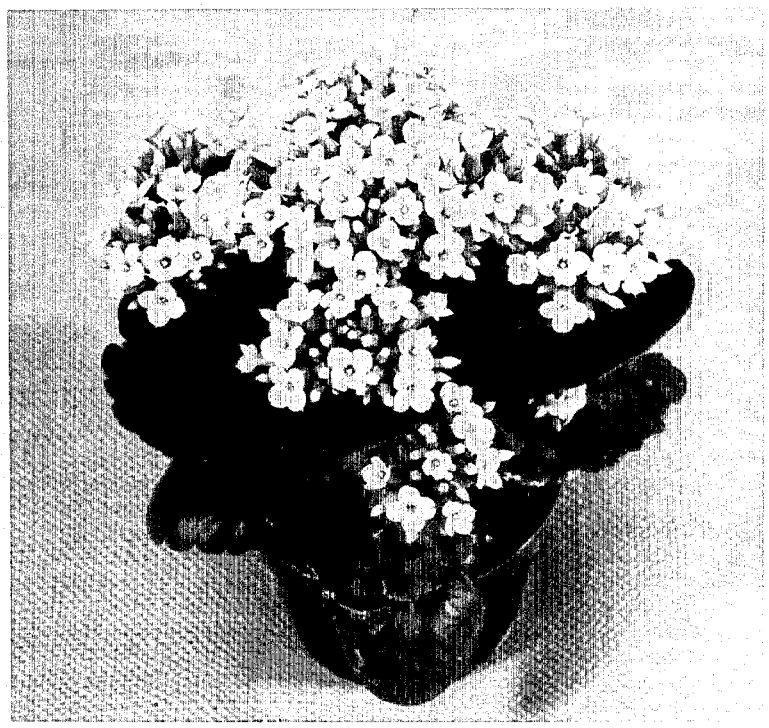

* * * * *